US012318778B2

(12) United States Patent
Chen et al.

(10) Patent No.: US 12,318,778 B2
(45) Date of Patent: Jun. 3, 2025

(54) MICROFLUIDIC CHIP SYSTEM AND METHOD FOR PREPARING DROPLETS

(71) Applicant: Qingdao MGI Tech Co., Ltd, Qingdao (CN)

(72) Inventors: I-Jane Chen, Shenzhen (CN); Tao Wu, Shenzhen (CN); Michael Junkin, San Jose, CA (US)

(73) Assignee: Qingdao MGI Tech Co., Ltd, Qingdao (CN)

( * ) Notice: Subject to any disclaimer, the term of this patent is extended or adjusted under 35 U.S.C. 154(b) by 981 days.

(21) Appl. No.: 17/209,463

(22) Filed: Mar. 23, 2021

(65) Prior Publication Data

US 2021/0205806 A1    Jul. 8, 2021

Related U.S. Application Data

(63) Continuation-in-part of application No. PCT/CN2019/108536, filed on Sep. 27, 2019.

(30) Foreign Application Priority Data

Sep. 29, 2018 (CN) .......................... 201811151625.2

(51) Int. Cl.
 *B01L 3/00* (2006.01)
 *C12Q 1/6806* (2018.01)
(52) U.S. Cl.
 CPC ..... *B01L 3/50273* (2013.01); *B01L 3/502753* (2013.01); *C12Q 1/6806* (2013.01);
 (Continued)
(58) Field of Classification Search
 None
 See application file for complete search history.

(56) References Cited

U.S. PATENT DOCUMENTS

2007/0161106 A1* 7/2007 Jervis .................... C12M 23/16
                                                              435/375
2015/0174576 A1   6/2015 Van Vilet et al.
                (Continued)

FOREIGN PATENT DOCUMENTS

CN     107418872 A    12/2017
CN     207271286 U  *  4/2018
                (Continued)

OTHER PUBLICATIONS

Zhang et al., (CN 107418872 A) translated description, Espacenet (Year: 2017).*

(Continued)

*Primary Examiner* — Paul S Hyun
*Assistant Examiner* — Mickey Huang
(74) *Attorney, Agent, or Firm* — ScienBiziP, P.C.

(57) ABSTRACT

A microfluidic chip system for generating droplets is provided by the present disclosure. The microfluidic chip system includes a droplet generation device for generating the droplets, a power generation device for supplying power to the droplet generation device, a collection container for collecting the droplets flowing out of the droplet generation device, a connection device connecting the droplet generation device, the power generation device, and the collection container to each other, and a preparation platform holds together the droplet generation device, the power generation device, and the collection container. A method for preparing the droplets is also provided by the present disclosure.

13 Claims, 12 Drawing Sheets

(52) U.S. Cl.
CPC ............. *B01L 2200/0647* (2013.01); *B01L 2300/0816* (2013.01); *B01L 2400/02* (2013.01); *B01L 2400/0433* (2013.01); *B01L 2400/0487* (2013.01)

(56) References Cited

U.S. PATENT DOCUMENTS

| | | | |
|---|---|---|---|
| 2015/0298157 A1* | 10/2015 | Weitz | ............... G10K 11/36 239/102.1 |
| 2017/0144116 A1 | 5/2017 | Ness et al. | |
| 2017/0144160 A1 | 5/2017 | Ness et al. | |
| 2018/0236443 A1 | 8/2018 | Masquelier et al. | |

FOREIGN PATENT DOCUMENTS

| | | | | |
|---|---|---|---|---|
| CN | 108080046 A | | 5/2018 | |
| CN | 108311178 A | | 7/2018 | |
| CN | 108364556 A | * | 8/2018 | |
| CN | 108393104 A | * | 8/2018 | ......... B01L 3/50273 |
| CN | 108499500 A | | 9/2018 | |
| JP | 2010025911 A | | 2/2010 | |
| JP | 2010506136 A | | 2/2010 | |
| WO | WO-2005059088 A1 | * | 6/2005 | ........... C12M 23/16 |

OTHER PUBLICATIONS

Lin et al., (CN 20727186 U) machine translation, USPTO, (Year: 2018).*

Ma et al., (CN 108393104 A) machine translation, USPTO, (Year: 2018).*

Zhu et al., (CN 108364556 A) machine translation, USPTO, (Year: 2018).*

* cited by examiner

MICROFLUIDIC CHIP SYSTEM AND METHOD FOR PREPARING DROPLETS

FIELD

The subject matter relates to single cell gene sequencing, and more particularly, to a microfluidic chip system and a method for preparing droplets.

BACKGROUND

Single cell genomics have developed rapidly in recent years, which reveal important clues in complex biological systems, including ecological diversity of microbial communities and genome of human cancers.

Microfluidic chips may be used in single cell sequencing, which also requires single cell sample preparation platforms for preparing droplets. The existing platforms are well suited for the preparation of the droplets, and are automated. However, these platforms are complex, requiring not only at least three pumps as power sources for generating flows and droplets, but also other devices and systems connected to the pumps. The pumps of the platform need to synchronously operate to ensure consistent flows of three reagents, otherwise the formation or the size uniformity of the droplets may be affected. Also, a decrease in pressure on a droplet generation device, flow velocities of continuous phase and dispersed phase, and a frequency for generating the droplets are not completely predictable, programmable, or reproducible.

In addition, the single cell sample preparation platform has a large size, is not easy to carry, and also has high requirements of its environment.

DETAILED DESCRIPTION

In order to be able to understand the features and advantages of the embodiments of the present disclosure, implementations are described, by way of embodiments only, with reference to the figures.

Referring to FIGS. 1 to 6, a first embodiment of a microfluidic chip system 100 is provided according to the present disclosure. The microfluidic chip system 100 can prepare droplets 200.

Figure 1:
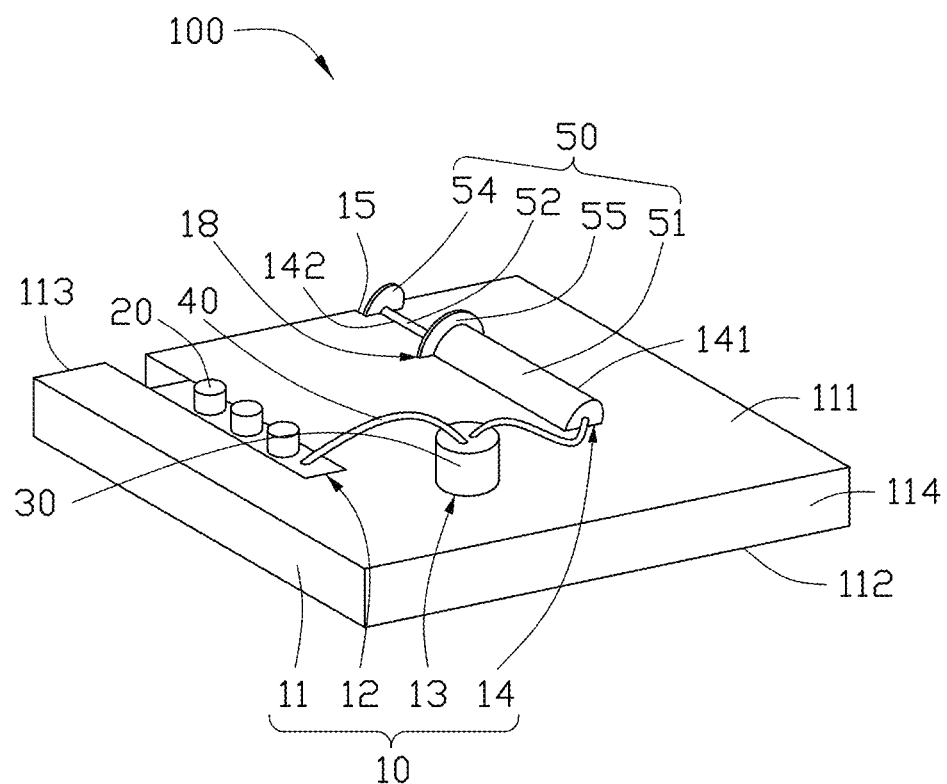
FIG. 1 is an isometric view of a microfluidic chip system in a first embodiment according to the present disclosure.
Figure 2:
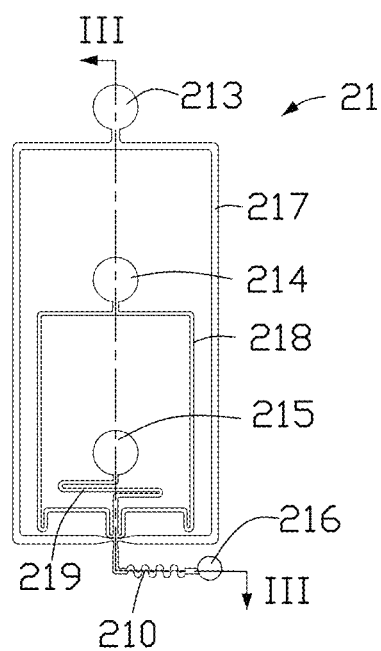
FIG. 2 is a diagrammatic view showing an internal structure of a main chip of the microfluidic chip system of FIG. 1.

Referring to FIG. 1, the microfluidic chip system 100 includes a preparation platform 10, a droplet generation device 20, a collection container 30, a connection device 40, and a power generation device 50. The preparation platform 10 supports and holds the droplet generation device 20, the collection container 30, the connection device 40, and the power generation device 50. The droplet generation device 40 can generate the droplets 200. The collection container 30 can collect the droplets 200 flowing out of the droplet generation device 20. The connection device 40 can connect the droplet generation device 20 to the collection container 30, and/or connect the droplet generation device 20 to the power generation device 50, and/or connect the power generation device 50 to the collection container 30. In the embodiment, the preparation platform 10 fixes the droplet generation device 20, the collection container 30, the connection device 40, and the power generation device 50 thereon. The term "fix" includes two meanings, one is that the droplet generation device 20, the collection container 30, and the power generation device 50 cannot be separated from the preparation platform 10, the other is that the droplet generation device 20, the collection container 30, and power generation device 50 can be separated from the preparation platform 10. In the embodiment, the droplet generation device 20, the collection container 30, and the power generation device 50 can be separated from the preparation platform 10.

In the embodiment, the droplet generation device 20, the collection container 30, and the power generation device 50 are all fixed on the preparation platform 10. The connection device 40 connects the droplet generation device 20 to the collection container 30, and further connects the collection container 30 to the power generation device 50. In detail, the preparation platform 10 includes a base 11, and a droplet generation device slot 12, a collection container slot 13, and a power generation device slot 14 on the base 11. The droplet generation device 20, the collection container 30, and the power generation device 50 are fixedly and respectively received in the droplet generation device slot 12, the collection container slot 13, and the power generation device slot 14.

In other embodiments, the droplet generation device 20, the collection container 30, and the power generation device 50 may also be arranged or mounted on the base 11 in other ways. For example, the base 11 may include a buckle device or a locking device. The droplet generation device 20, the collection container 30, and the power generation device 50 may be mounted on the base 11 through a buckle or locking mechanism.

In yet other embodiments, the collection container 30 may also be disposed on and integrally formed with the droplet generation device 20. For example, the upper surface of the droplet generation device 20 may extend upwards to form the collection container 30. Then, the preparation platform 10 only needs to fix the droplet generation device 20, the connection device 40, and the power generation device 50 thereon.

In detail, the base 11 includes a first surface 111, a second surface 112 opposite to the first surface 111, a first sidewall 113 connected between the first surface 111 and the second surface 112, and a second sidewall 114 opposite to the first sidewall 113. Each of the droplet generation device slot 12 and the power generation device slot 14 is recessed from the first surface 111 and the first sidewall 113 to the second surface 112 and the second sidewall 114. The collection container slot 13 is recessed from the first surface 111 to the second surface 112. In detail, each of the droplet generation device slot 12 and the power generation device slot 14 passes through the first surface 111 and the first sidewall 113. The collection container slot 13 passes through the first surface 111 only.

In other embodiments, the droplet generation device slot 12 and the power generation device slot 14 may pass through the first surface 111 only.

The preparation platform 10 can be formed by, but is not limited to, a 3D printing method. In the embodiment, the preparation platform 10 is formed by the 3D printing method. The cost is low, and the size of the preparation platform 10 can be adjusted as needed.

In the embodiment, the power generation device slot 14 includes a first receiving portion 141 and a second receiving portion 142. The first receiving portion 141 can receive therein a main body 51 of the power generation unit 50 (see FIG. 1 and following description). The second receiving portion 142 can receive therein an operation portion 52 of the power generation unit 50 (see FIG. 1 and following description).

The preparation platform 10 also includes a first limiting slot 15 and a second limiting slot 18. The first limiting slot 15 can fixedly receive therein a first limiting member 54 of the power generation device 50 (see FIG. 1 and following description), thereby holding the operation portion 52 in a predetermined position. The second limiting slot 18 connects to the power generation device slot 14, and can fixedly receive therein a second limiting member 55 of the power generation device 50 (see FIG. 1 and following description).

In the embodiment, the first limit groove 15 is recessed from the first surface 111 and the first sidewall 113 to the second surface 112 and the second sidewall 114. In other embodiments, the first sidewall 113 may also have the limiting function of the first limiting slot 15. The first limiting slot 15 may also pass through the first surface 111 but not the first sidewall 113.

The droplet generation device 20 includes a chip body 21. The chip body 21 defines a continuous phase inlet and a dispersed phase inlet. The chip body 21 also defines a continuous phase guiding channel, a dispersed phase guiding channel, and a converging channel therein. The continuous phase inlet connects to the continuous phase guiding channel. The dispersed phase inlet connects to the dispersed phase guiding channel. The continuous phase guiding channel and the dispersed phase guiding channel interconnect with each other, and they further connect to an end of the converging channel. A continuous phase enters the continuous phase guiding channel through the continuous phase inlet. A dispersed phase enters the dispersed phase guiding channel through the dispersed phase inlet. The continuous phase and the dispersed phase converge at an intersection of the continuous phase guiding channel and the dispersed phase guiding channel, and further enter the converging channel.

The continuous phase can be oil phase. The dispersed phase can be cell fluid, microsphere fluid, or water. In the embodiment, the continuous phase is the oil phase, and the dispersed phase includes the cell fluid and the microbead fluid.

In the embodiment, the chip body 21 includes a third surface 211 and a fourth surface 212 opposite to the third surface 211. The third surface 211 is recessed towards the fourth surface 212 to form an oil phase inlet 213 (continuous phase inlet), a cell fluid inlet 214 (dispersed phase inlet), a microbead fluid inlet 215 (dispersed phase inlet), and a droplet outlet 216. Each of the oil phase inlet 213, the cell fluid inlet 214, the microbead fluid inlet 215, and the droplet outlet 216 passes through only the third surface 211. In other embodiments, the droplet outlet 216 may also be defined on one of the sidewalls between the third surface 211 and the fourth surface 212.

The chip body 21 also defines an oil phase guiding channel 217 (continuous phase guiding channel), a cell fluid guiding channel 218 (dispersed phase guiding channel), and a microbead fluid guiding channel 219 (dispersed phase guiding channel). The oil phase inlet 213 connects to the droplet outlet 216 through the oil phase guiding channel 217.

The cell fluid inlet 214 connects to the droplet outlet 216 through the cell fluid guiding channel 218. The microbead fluid inlet 215 connects to the droplet outlet 216 through the microbead fluid guiding channel 219.

The chip body 21 also defines a converging channel 210. The oil phase guiding channel 217, the cell fluid guiding channel 218, and the microbead fluid guiding channel 219 intersect at one end of the converging channel 210. The other end of the converging channel 210 connects to the droplet outlet 213.

In the embodiment, two oil phase guiding channels 217, two cell fluid guiding channels 218, and one microbead fluid guiding channels 219 are defined in the chip body 21. In detail, the two oil phase guiding channels 217 surround the cell fluid inlet 214 and the two cell fluid guiding channels 218. The two cell fluid guiding channels 218 surround the microbead fluid inlet 215 and the microbead fluid guiding channels 219. Before the interconnection of the oil phase guiding channel 217, the cell fluid guiding channel 218, and the microbead fluid guiding channel 219, the two oil phase guiding channel 217 and the two cell fluid guiding channel 218 are symmetrically disposed on two sides of the microbead fluid guiding channel 219.

In the embodiment, the oil phase inlet 213, the cell fluid inlet 214, and the microbead fluid inlet 215 are disposed on a single straight line.

In the embodiment, the oil phase inlet 213, the cell fluid inlet 214, the microbead fluid inlet 215, and the droplet outlet 216 are not disposed on a single straight line.

The microfluidic chip system 100 can also include a continuous phase reservoir and a dispersed phase reservoir. The continuous phase reservoir connects to the continuous phase inlet. The dispersed phase reservoir connects to the dispersed phase inlet. The continuous phase reservoir and the dispersed phase reservoir can be disposed on or outside the chip body 21.

Figure 3:
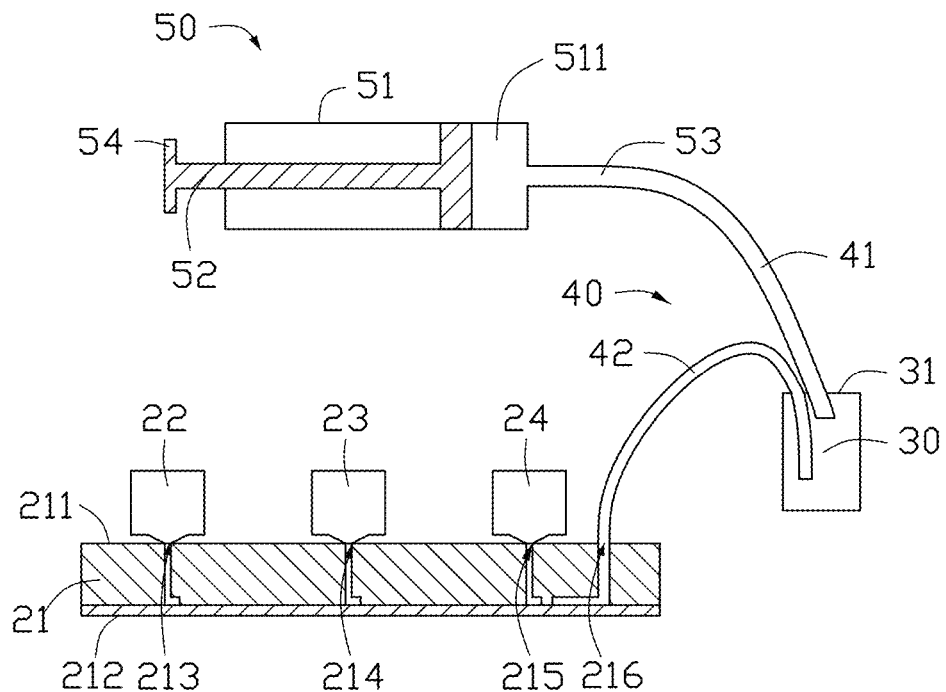
FIG. 3 is a diagrammatic view showing a microfluidic chip, a collection container, and a power generation device of the microfluidic chip system of FIG. 1, in which the power generation device and the chip body are shown by a cross-sectional view (along III-III of FIG. 2).
Figure 4:
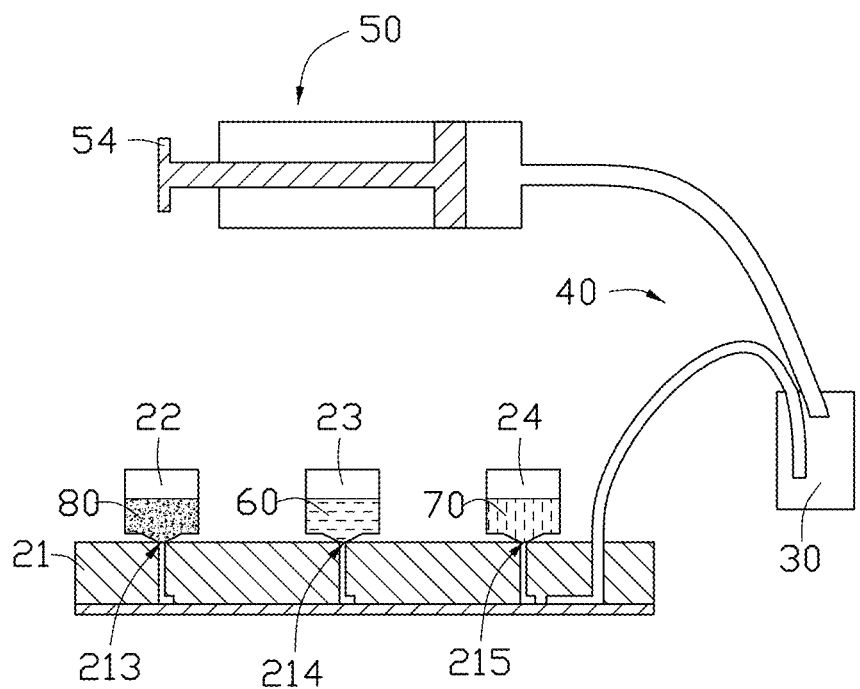
FIG. 4 is a diagrammatic view showing oil phase, cell fluid, and microbead fluid added into a first reservoir, a second reservoir, and a third reservoir of the microfluidic chip of FIG. 3.
Figure 5:
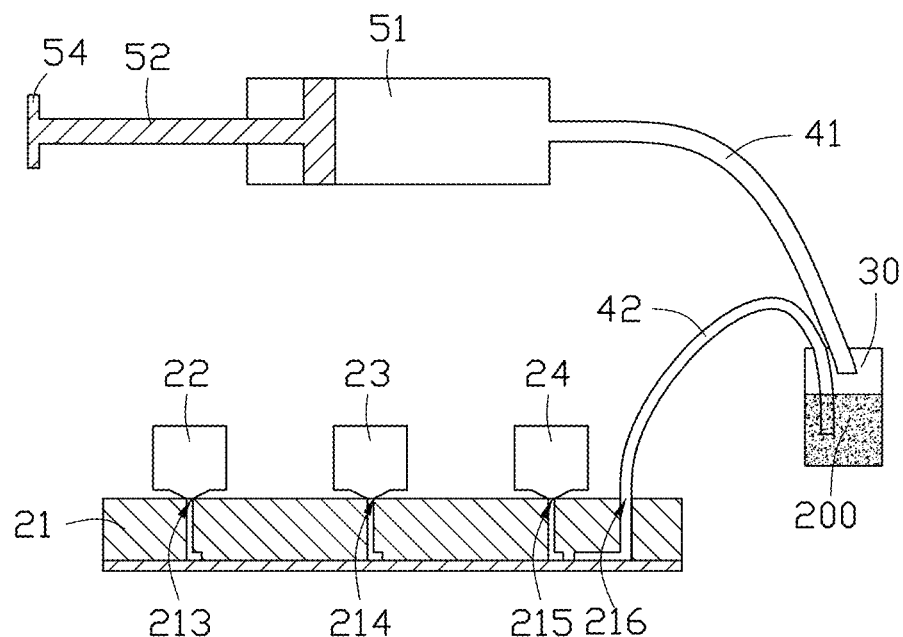
FIG. 5 is a diagrammatic view showing the power generating device of the microfluidic chip system of FIG. 4 generating a vacuum.

In detail, referring to FIG. 3, in the embodiment, the microfluidic on-chip system 100 includes a first reservoir 22 (continuous phase reservoir), a second reservoir 23 (dispersed phase reservoir), and a third reservoir 24 (dispersed phase reservoir). The first reservoir 22 connects to the oil phase inlet 213. The second reservoir 23 connects to the cell fluid inlet 214. The third reservoir 24 connects to the microbead fluid inlet 215.

In the embodiment, the first reservoir 22, the second reservoir 23, and the third reservoir 24 are disposed on the chip body 21. In detail, the chip body 21 is integrally formed with the first reservoir 22, the second reservoir 23, and the third reservoir 24. In other embodiments, the first reservoir 22, the second reservoir 23, and the third reservoir 24 may also be respectively inserted into the oil phase inlet 213, the cell fluid inlet 214, and the microbead fluid inlet 215.

In the embodiment, the first reservoir 22 can temporarily store oil phase 80. A storage volume of the first reservoir 22 may be, but is not limited to, 100 µL, 200 µL, 500 µL, or 1 mL.

In the embodiment, the second reservoir 23 can temporarily store cell fluid 60. A storage volume of the second reservoir 23 may be, but is not limited to, 100 µL, 200 µL, 500 µL, or 1 mL.

In the embodiment, the third reservoir 24 can temporarily store microbead fluid 70. A storage volume of the third reservoir 24 may be, but is not limited to, 100 µL, 200 µL, 500 µL, or 1 mL.

The microbead fluid 70 can be one of polystyrene microbead fluid, resin microbead fluid, and magnetic bead solution.

An opening (not shown) is formed on each of the first reservoir 22, the second reservoir 23, and the third reservoir 24, to facilitate the respective transfers of the oil phase 80, the cell fluid 60, and the microbead fluid 70 to the first reservoir 22, the second reservoir 23, and the third reservoir 24.

A volume ratio of the oil phase 80, cell fluid 60, and microbead fluid 70 in the first reservoir 22, the second reservoir 23, and the third reservoir 24 can be, but is not limited to, 2:1:1. In the embodiment, the volume of the cell fluid 60 is 200 µL, the volume of the microbead fluid 70 is 200 µL, and the volume of the oil phase 80 is 400 mL.

In other embodiments, the first reservoir 22, the second reservoir 23, and the third reservoir 24 may be absent from the droplet generation device 20. Then, the oil phase 80 may be directly added to the oil phase inlet 213, the cell fluid 60 may be directly added to the cell fluid inlet 214, and the microbead fluid 70 may be directly added to the microbead fluid inlet 215.

The collection container 30 can collect the droplets 200. The collection container 30 includes a cover 31, on which two through holes (not shown) are defined. The cover 31 is connected separably or inseparably with the main body of the collection container 30.

A volume of the collection container 30 can be, but is not limited to, 1 mL or 5 mL. In the embodiment, the volume of the collection container 30 is 1 mL.

In the embodiment, the connection device 40 includes a first pipe 41 and a second pipe 42. One end of the first pipe 41 connects to the power generation device 50, and the other end connects to the collection container 30. One end of the second pipe 42 connects to the chip body 21 and the droplet outlet 216, and the other end connects to the collection container 30.

In detail, in the embodiment, one end of the second pipe 42 connects to the third surface 211, and the other end connects to the collecting container 30 through a through hole in the cover 31 of the collecting container 30. One end of the first pipe 41 connects to the power generation device 50, and the other end connects to the collecting container 30 through another through hole of the cover 31.

In the embodiment, each of the first pipe 41 and the second pipe 42 is a 10 cm long hose.

The power generation device 50 provides power for the droplet generation device 20 to generate the droplets 200, to cause the oil phase 80, the cell fluid 60, and the microbead fluid 70 in the first reservoir 22, the second reservoir 23, and the third reservoir 24 to flow inside the oil phase guiding channel 217, the cell fluid guiding channel 218, and the microbead fluid guiding channel 219, and further to converge in the converging channel 210 to form the droplets 200. The droplets 200 flow out of the droplet outlet 216 and enters the collection container 30.

In the embodiment, the power generation device 50 is a negative pressure generation device. The power generation device 50 includes a main body 51, an operation portion 52, and a gas inlet and outlet terminal 53. The main body 51 defines a receiving space 511. One end of the operation portion 52 is received in the receiving space 511, and the other end is exposed from the main body 51. The end of the operation portion 52 in the receiving space 511 is closely attached on an inner wall of the receiving space 511. When an external force is applied on the end of the operation portion 52 exposed from the main body 51, the operation portion 52 can slide in the receiving space 511. The gas inlet and outlet terminal 53 is disposed on an end of the operation portion 52 away from the exposed main body 51, and connects to the receiving space 511. One end of the second pipe 42 away from the collection container 30 connects to the gas inlet and outlet terminal 53.

In detail, in the embodiment, the power generation device 50 is an injection device.

In the embodiment, the power generation device 50 also includes a first limiting member 54 and a second limiting member 55. The first limiting member 54 is arranged at an end of the operation portion 52 exposed from the main body 51. The first limiting member 54 and the first limiting slot 15 cooperate with each other to pull the operation portion 52 to a predetermined position, thereby maintaining a vacuum inside the power generation device 50. The second limiting member 55 is fixed on the main body 51. The second limiting member 55 and the second limiting slot 18 cooperate with each other to limit a movement of the main body 51 when the operation portion 52 is pulled.

When the operation portion 52 is moved under the external force to cause the first limiting member 52 to move and be limited in first limiting slot 15, an initial volume $V_1$ of the second pipe 42, the collection container 30, the first pipe 41, and the droplet outlet 216, the converging channel 210, the microbead fluid guiding channel 219, the cell fluid guiding channel 218, and the oil phase guiding channel 217 of the chip body 21 increases to volume $V_2$. According to an ideal gas state equation $P_1V_1=P_2V_2$ (wherein $P_1$ and $P_2$ respectively denote pressures corresponding to the initial volume $V_1$ and the volume $V_2$), the pressure in the second pipe 42, the collection container 30, the first pipe 41, and the droplet outlet 216, the converging channel 210, the microbead fluid guiding channel 219, the cell fluid guiding channel 218, the oil phase guiding channel 217, the first reservoir 22, the second reservoir 23, and the third reservoir 24 of the chip body 21 is less than atmospheric pressure. The difference in pressure drives the dispersed phase and the continuous phase in the droplet generation device 20 to flow into the collection container 30 in the form of droplets.

The power generation device 50 can also generate power in other ways. 1) The power is generated in a closed container before the power generation device 50 connects to the chip body 21. 2) The power is generated by the power generation device 50 that is driven by a pump. 3) The power is generated by pulling or pushing a plunger of a syringe (or a similar device).

In some embodiments, the microfluidic chip system 100 may also include at least one vibration device. The vibration device is disposed to correspond to the third reservoir and/or the second reservoir, for causing the microbead fluid 70 and/or the cell fluid 60 to be vibrated and agitated.

Figure 6:
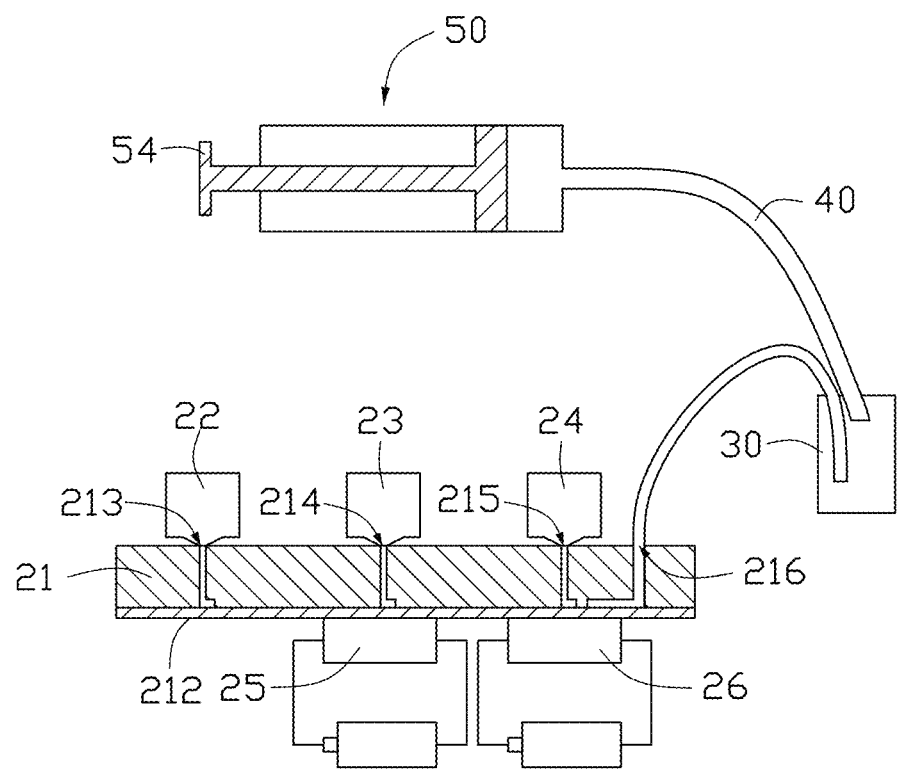
FIG. 6 is a diagrammatic view of a microfluidic chip system including a vibration device.

Referring to FIG. 6, the microfluidic chip system 100 also includes at least one vibration device for generating vibration to the dispersed phase.

In detail, in the embodiment, the microfluidic chip system 100 includes a first vibration device 25 and a second vibration device 26. The first vibration device 25 and the second vibration device 26 are fixed in the droplet generation device slot 12, and correspond to the cell fluid inlet 214 and the microbead fluid inlet 215.

Each of the first vibration device 25 and the second vibration device 26 can be a ceramic oscillating plate.

The first vibration device 25 and the second vibration device 26 vibrate on activation. The vibration is applied on the cell fluid 60 and the microbead fluid 70, which decreases cell or microbead sedimentation in the microbead fluid 70 and the cell fluid 60 during experiments, thereby ensuring a homogenous concentration in each of the microbead fluid 70 and the cell fluid 60.

In other embodiments, the first vibration device 25 and the second vibration device 26 may also be disposed on the chip body 21. For example, the first vibration device 25 and the second vibration device 26 can be disposed on the fourth surface 212 of the chip body 21, and correspond to the cell fluid inlet 214 and the microbead fluid inlet 215, respectively. The first vibration device 25 and the second vibration device 26 may also be disposed on the sidewall between the third surface 211 and the fourth surface 212 of the chip body 21, and correspond to the cell fluid inlet 214 and the microbead fluid inlet 215, respectively. The positions of the first vibration device 25 and the second vibration device 26 are to ensure that the vibration can be applied to the cell fluid 60 and microbead fluid 70 to decrease the cell or microbead sedimentation in the cell fluid 60 and the microbead fluid 70.

In another embodiment, the microfluidic chip system 100 may include only one vibration device, for example, the second vibration device 26. The second vibration device 26 may be fixed in the droplet generation device slot 12 to correspond to the microbead fluid inlet 215. The second vibration device 26 may also be fixed on the fourth surface 212 of the chip body 21 to correspond to the microbead fluid inlet 215. Thus, microbead sedimentation in the microbead fluid 70 can be decreased during experiments, and homogenous concentrations in the microbead fluid 70 can be ensured.

In yet another embodiment, the microfluidic chip system 100 may include only one vibration device corresponding to each of the cell fluid inlet 214 and the microbead fluid inlet 215. The vibration device simultaneously applies vibration on the cell fluid 60 and the microbead fluid 70.

When the power is applied to the power generation device 50, a vacuum is formed inside the power generation device 50, which drives the dispersed phase and the continuous phase to flow in the chip body 10. Because the power generation device is an injection device, vacuum can be generated through a simple action. When reagents (continuous phase and dispersed phase) begin to flow in the chip body, the volume of air in the power generation device in positive pressure or negative pressure system will expand or be compressed, which can lead to a smaller difference in pressure between the chip inlet (continuous phase inlet and dispersed phase inlet) and the chip outlet (droplet outlet), thereby slowing down the flow velocity of reagents. The change of the flow velocity of reagent results in change of size of the droplets. Therefore, the pressure change in the chip body 10, the flow velocity of the dispersed phase and the continuous phase, the size and the generation frequency of the droplet become predictable, programmable, and reproducible.

Figure 7:
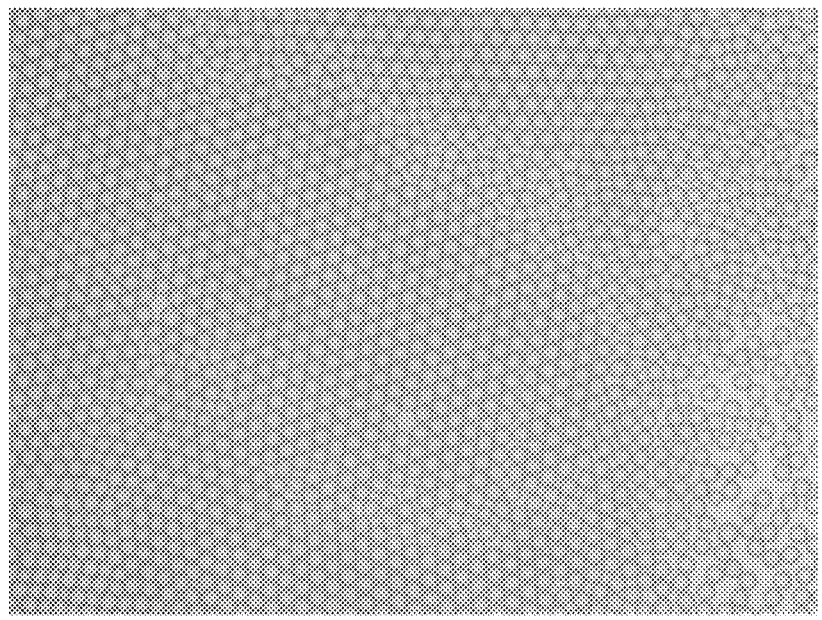
FIG. 7 is a diagrammatic view of droplets (not including microbeads and cells) generated by the microfluidic chip system.

FIG. 7 is a diagrammatic view showing the droplets (no microbead or cell is included) generated by the microfluidic chip system according to the present disclosure. According to FIG. 7, the droplets generated by the microfluidic chip system 100 of the present disclosure have a small variation in size and the droplets are highly uniform. In the embodiment, the size of the droplets is 55.7 µm, varying in size by only 2%.

Figure 8:
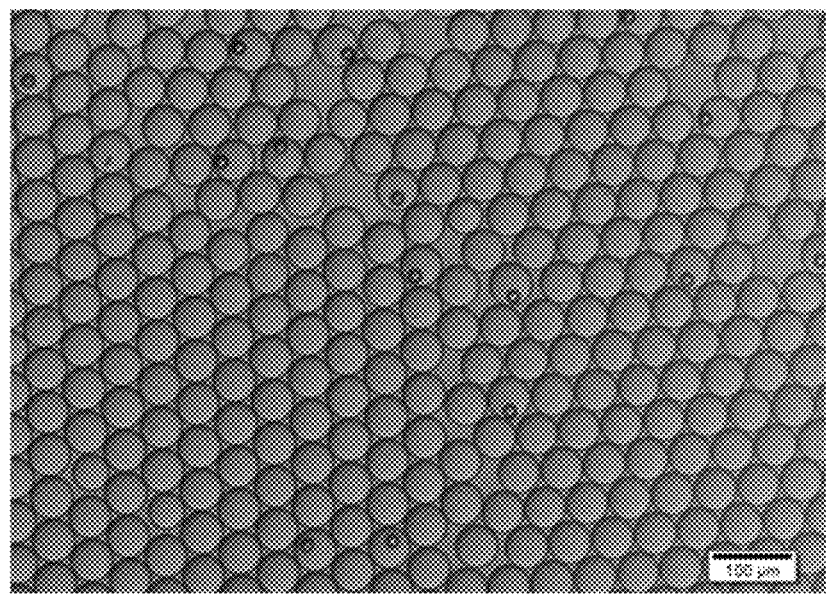
FIG. 8 is a diagrammatic view of droplets (including microbeads and cells) generated by the microfluidic chip system.

FIG. 8 is a diagrammatic view showing the droplets (microbeads and cells included) generated by the microfluidic chip system according to the present disclosure. According to FIG. 8, the microfluidic chip system according to the present disclosure can wrap the microbeads and cells in the oil phase.

Figure 9:
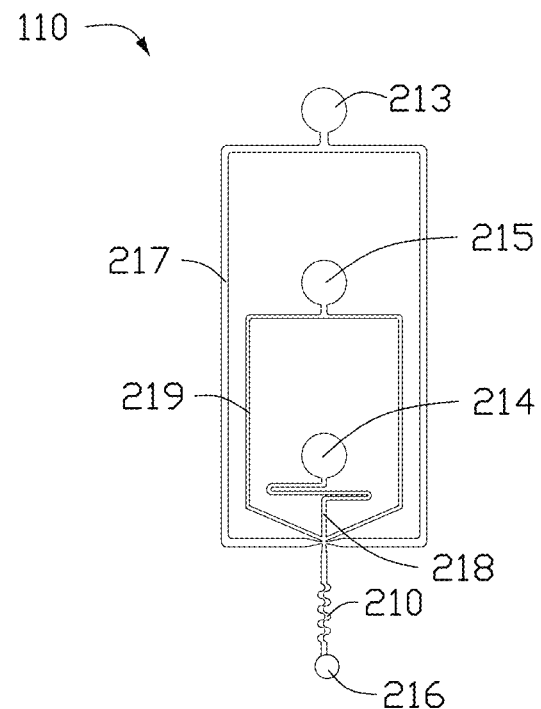
FIG. 9 is a diagrammatic view showing an internal structure of the chip body in a second embodiment according to the present disclosure.

FIG. 9 shows an internal structure of a chip body 110 in a second embodiment according to the present disclosure. The internal structure of the chip body 110 is substantially the same as that of the first embodiment of the chip body 21. The difference is that there are two oil phase guiding channels 217, one cell fluid guiding channel 218, and two microbead fluid guiding channels 219 defined in the chip body 110. In detail, the two oil phase guiding channels 217 surround the microbead fluid inlet 215 and the two microbead fluid guiding channels 219. The two microbead fluid guiding channels 219 surround the cell fluid inlet 214 and the cell fluid guiding channel 218. Before interconnection of the oil phase guiding channel 217, the cell fluid guiding channel 218, and the microbead fluid guiding channel 219, the two oil phase guiding channels 217 and the two microbead fluid guiding channels 219 are symmetrically disposed on both sides of the microbead fluid guiding channel 219.

In the embodiment, the oil phase inlet 213, the cell fluid inlet 214, the microbead fluid inlet 215, and the droplet outlet 216 are disposed on a single straight line.

Figure 10:
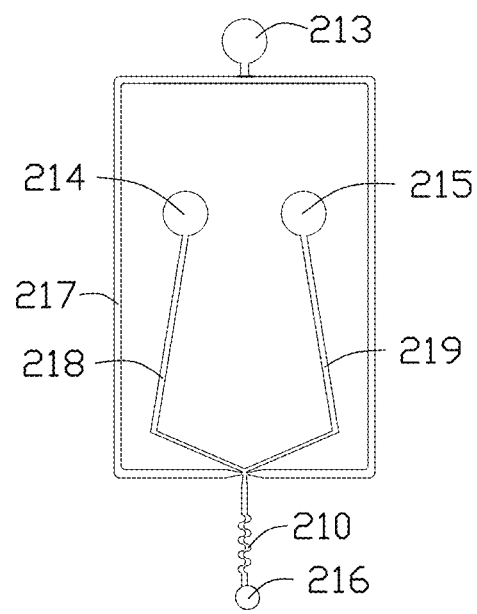
FIG. 10 is a diagrammatic view showing an internal structure of the chip body in a third embodiment according to the present disclosure.

FIG. 10 is a diagrammatic view showing an internal construction of a chip body 120 in a third embodiment according to the present disclosure. The internal structure of the chip body 120 is substantially the same as that of the first embodiment of the chip body 21. The difference is that there are two oil phase guiding channels 217, one cell fluid guiding channel 218, and one microbead fluid guiding channel 219 defined in the chip body 120. In detail, the two oil phase guiding channels 217 surround the microbead fluid inlet 215, the microbead fluid guiding channel 219, the cell fluid inlet 214, and the cell fluid guiding channel 218. The cell fluid guiding channel 218 and the microbead fluid guiding channel 219 are symmetrical with each other. The two oil phase leading guiding channels 217 are disposed on both sides of the cell fluid guiding channel 218 and the microbead fluid guiding channel 219.

In the embodiment, the oil phase inlet 213 and the droplet outlet 216 are disposed on a single straight line. The oil phase inlet 213, the cell fluid inlet 214, the microbead fluid inlet 215, and the droplet outlet 216 are not disposed on the single straight line.

Figure 11:
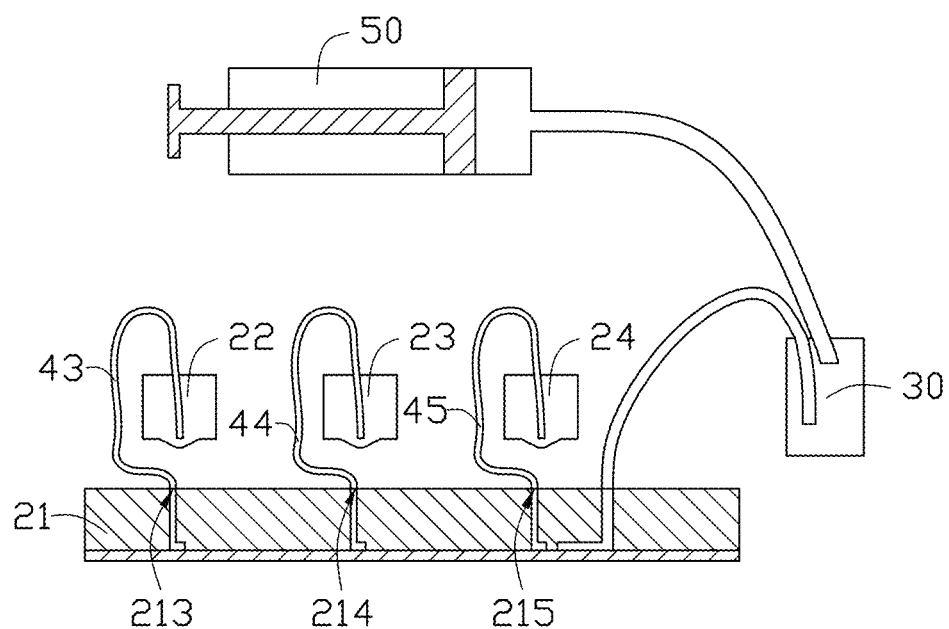
FIG. 11 is a diagrammatic view showing connections among a microfluidic chip, a collection container, and a power generation device in a fourth embodiment according to the present disclosure, in which the power generation device and the chip body are shown in cross-sectional view.

FIG. 11 shows the connections among the chip body 21, the collection container 30, and the power generation device 50 in a fourth embodiment according to the present disclosure. The cross-section of the power generation device 50 is shown. In the embodiment, the connections among the chip body 21, the collection container 30, and the power generation device 50 are substantially the same as those among the chip body 21, the collection container 30, and the power generation device 50 shown in FIG. 3. The only difference is that the first reservoir 22, the second reservoir 23, and the third reservoir 24 are disposed outside the chip body 21, and these hermetically connect respectively to the oil phase inlet 213, the cell fluid inlet 214, and the microbeads fluid inlet 215 through a third pipe 43, a fourth pipe 214, and a fifth pipe 42.

Figure 12:
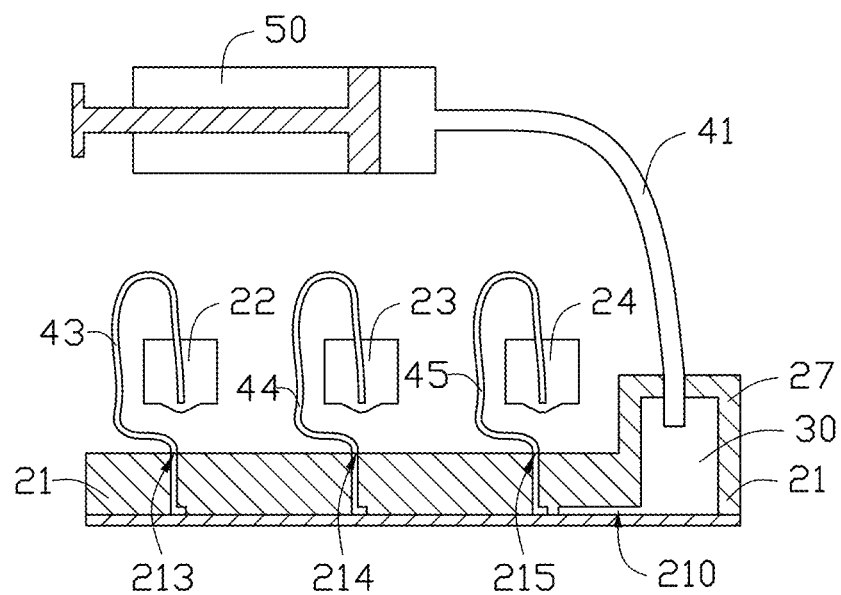
FIG. 12 is a diagrammatic view showing connections among a microfluidic chip, a collection container, and a power generation device in a fifth embodiment according to the present disclosure, in which the power generation device and the chip body are shown in cross-sectional view.

FIG. 12 is a diagrammatic view showing the connections among the chip body 21, the collection container 30, and the power generation device 50 in a fifth embodiment according to the present disclosure. The cross-sectional view of the power generation device 50 is shown. In the embodiment, the connections among the chip body 21, the collection container 30, and the power generation device 50 are substantially the same as those among the chip body 21, the collection container 30, and the power generation device 50 shown in FIG. 9. The difference is that the droplet generation device 20 further includes a protrusion 27 formed on the chip body 21. The collection container 30 is disposed in the protrusion 27. The converging channel 210 connects to the collection container 30. The collection container 30 hermetically connects to the power generation device 50 through the first pipe 41.

Figure 13:
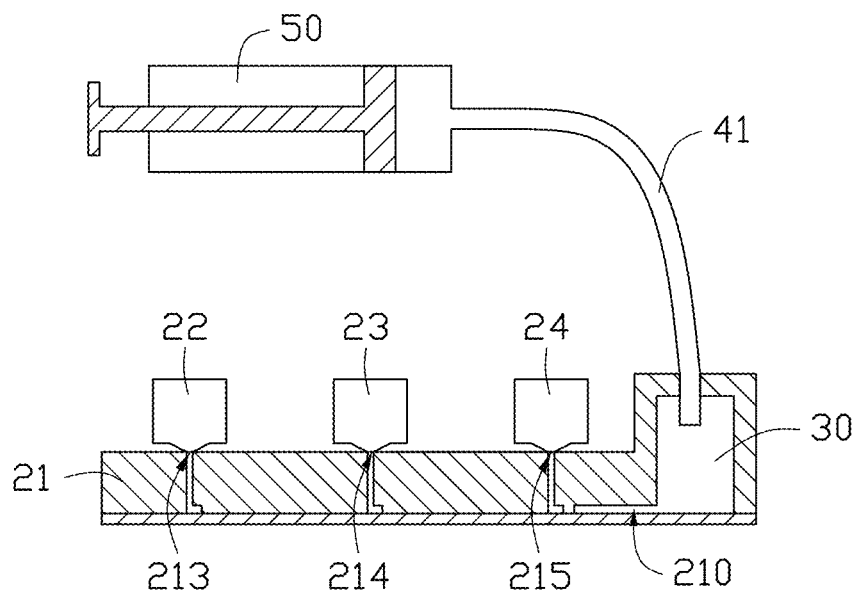
FIG. 13 is a diagrammatic view showing connections among a microfluidic chip, a collection container, and a power generation device in a sixth embodiment according to the present disclosure, in which the power generation device and the chip body are shown in cross-sectional view.

FIG. 13 is a diagrammatic view showing the connections among the chip body 21, the collection container 30, and the power generation device 50 in a sixth embodiment according to the present disclosure. The cross-sectional view of the power generation device 50 is shown. In the embodiment, the connections among the chip body 21, the collection container 30, and the power generation device 50 are substantially the same as those among the chip body 21, the collection container 30, and the power generation device 50 shown in FIG. 12. The difference is that the first reservoir 22, the second reservoir 23, and the third reservoir 24 are disposed on the chip body 21. The first reservoir 22 hermetically connects to the oil phase reservoir inlet 213, the second reservoir 23 hermetically connects to the cell fluid inlet 214, and the third reservoir 24 hermetically connects to the microbeads fluid inlet 215.

Figure 14:
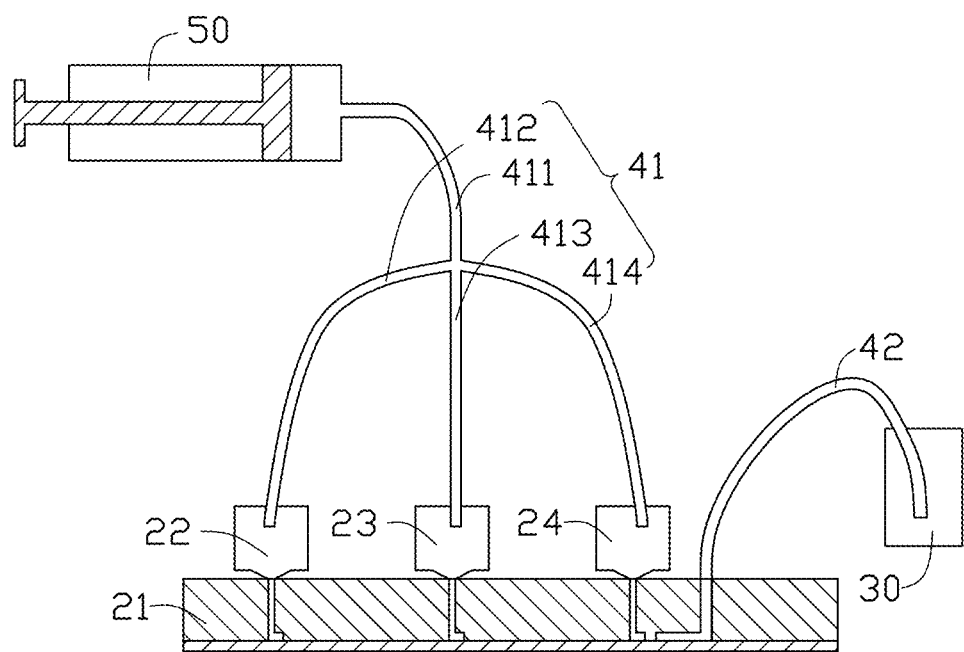
FIG. 14 is a diagrammatic view showing connections among a microfluidic chip, a collection container, and a power generation device in a seventh embodiment according to the present disclosure, in which the power generation device and the chip body are shown in cross-sectional view.

FIG. 14 shows the connections among the chip body 21, the collection container 30, and the power generation device 50 in a seventh embodiment according to the present disclosure. The cross-section of the power generation device 50 is shown. In the embodiment, the connections among the chip body 21, the collection container 30, and the power generation device 50 are substantially the same as those among the chip body 21, the collection container 30, and the power generation device 50 shown in FIG. 3. The difference is that the power generation device 50 is a positive pressure generation device. In detail, the power generation device 50 is an injection device. The power generation device 50 connects to the first reservoir 22, the second reservoir 23, and the third reservoir 24 through the first pipe 41. In the embodiment, the first pipe 41 is a bifurcated pipe having a plurality of contacts. In detail, the first pipe 41 includes a primary connection section 411, a first bifurcated connection section 412, a second bifurcated connection section 413, and a third bifurcated connection section 414. One end of the period of 411 hermetically connects to the gas inlet and outlet terminal 53 of the power generation device 50. The other end hermetically connects to the first bifurcated connection section 412, the second bifurcated connection section 413, and the third bifurcated connection section 414.

The structure in the embodiment is also applicable to the chip body as shown in FIGS. 9 and 10.

Figure 15:
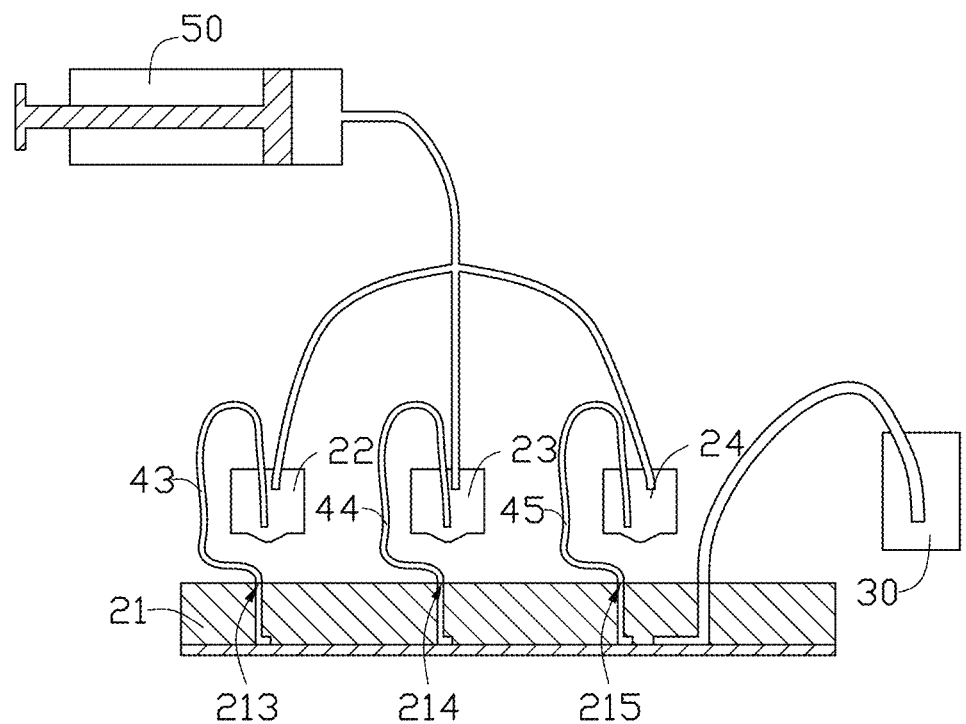
FIG. 15 is a diagrammatic view showing connections among a microfluidic chip, a collection container, and a power generation device in an eighth embodiment according to the present disclosure, in which the power generation device and the chip body are shown in cross-sectional view.

FIG. 15 shows the connections among the chip body 21, the collection container 30, and the power generation device 50 in an eighth embodiment according to the present disclosure. The cross-section of the power generation device 50 is shown. In the embodiment, the connections among the chip body 21, the collection container 30, and the power generation device 50 are substantially the same as those among the chip body 21, the collection container 30, and the power generation device 50 shown in FIG. 14. The difference is that the first reservoir 22, the second reservoir 23, and the third reservoir 24 are disposed outside the chip body 21, and these hermetically connect respectively to the oil phase inlet 213, the cell fluid inlet 214, and the microbeads fluid inlet 215 through a third pipe 43, a fourth pipe 214, and a fifth pipe 42.

Figure 16:
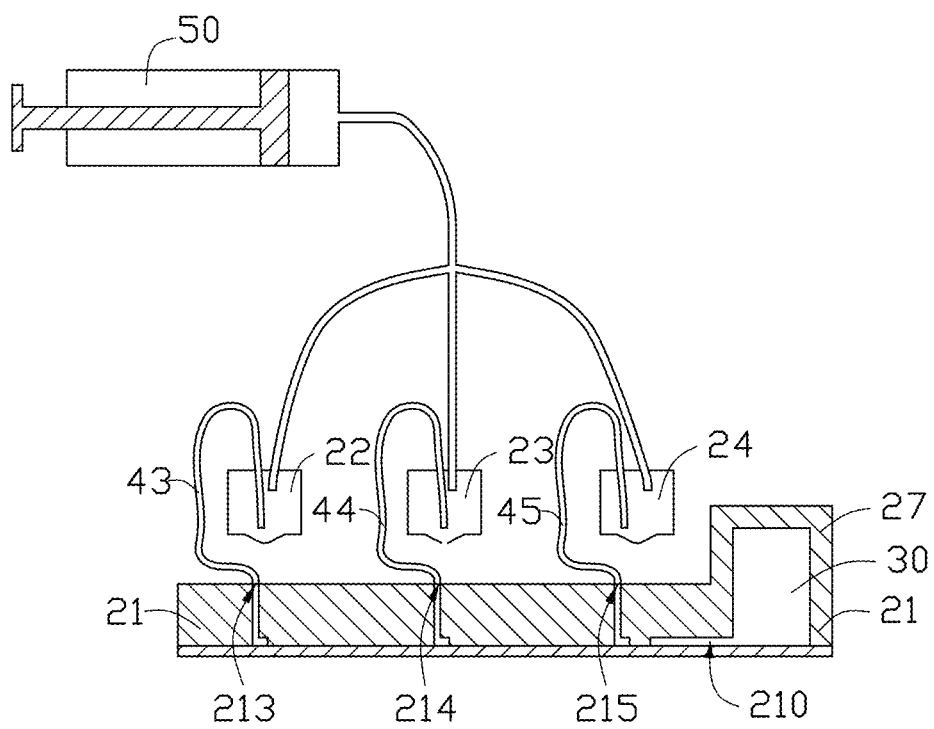
FIG. 16 a diagrammatic view showing connections among a microfluidic chip, a collection container, and a power generation device in a ninth embodiment according to the present disclosure, in which the power generation device and the chip body are shown in cross-sectional view.

FIG. 16 is a diagrammatic view showing the connections among the chip body 21, the collection container 30, and the power generation device 50 in a ninth embodiment according to the present disclosure. The cross-section of the power generation device 50 is shown. In the embodiment, the connections among the chip body 21, the collection container 30, and the power generation device 50 are substantially the same as those among the chip body 21, the collection container 30, and the power generation device 50 shown in FIG. 15. The difference is that the droplet generation device 20 further includes a protrusion 27 formed on the chip body 21. The collection container 30 is disposed in the protrusion 27. The converging channel 210 is connected to the collection container 30. The collection container 30 hermetically connects to the power generation device 50 through the first pipe 41.

Figure 17:
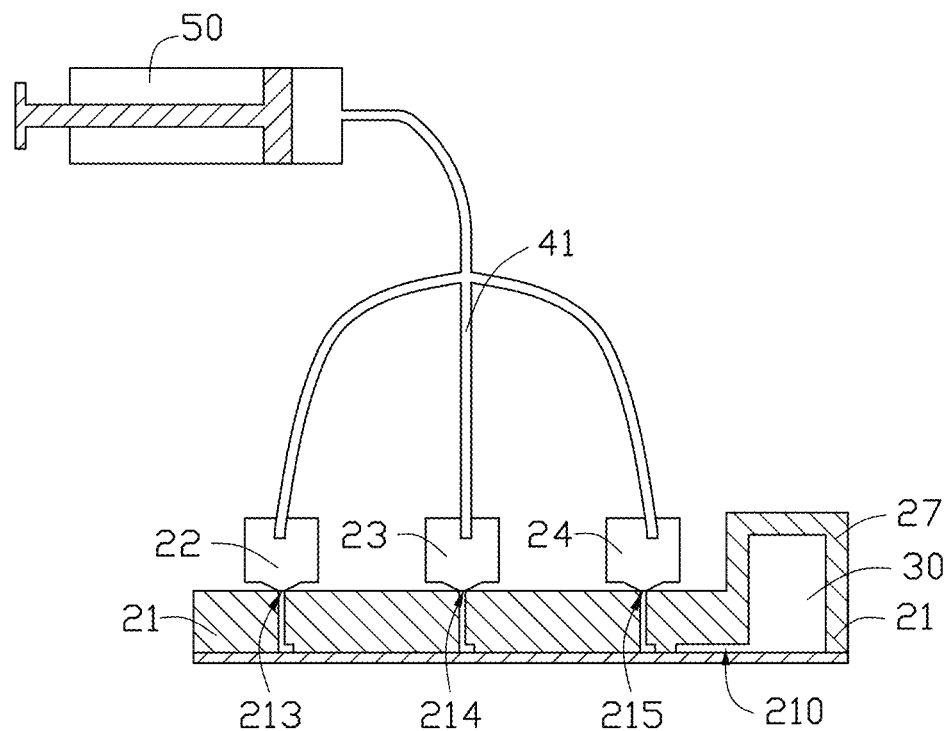
FIG. 17 is a diagrammatic view showing connections among a microfluidic chip, a collection container, and a power generation device in a tenth embodiment according to the present disclosure, in which the power generation device and the chip body are shown in cross-sectional view.

FIG. 17 is a diagrammatic view showing the connections among the chip body 21, the collection container 30, and the power generation device 50 in a tenth embodiment according to the present disclosure. The cross-section of the power generation device 50 is shown. In the embodiment, the connections among the chip body 21, the collection container 30, and the power generation device 50 are substantially the same as those among the chip body 21, the collection container 30, and the power generation device 50 shown in FIG. 16. The difference is that the first reservoir 22, the second reservoir 23, and the third reservoir 24 are disposed on the chip body 21. The first reservoir 22 hermetically connects to the oil phase reservoir inlet 213, the second reservoir 23 hermetically connects to the cell fluid inlet 214, and the third reservoir 24 hermetically connects to the microbeads fluid inlet 215.

Figure 18:
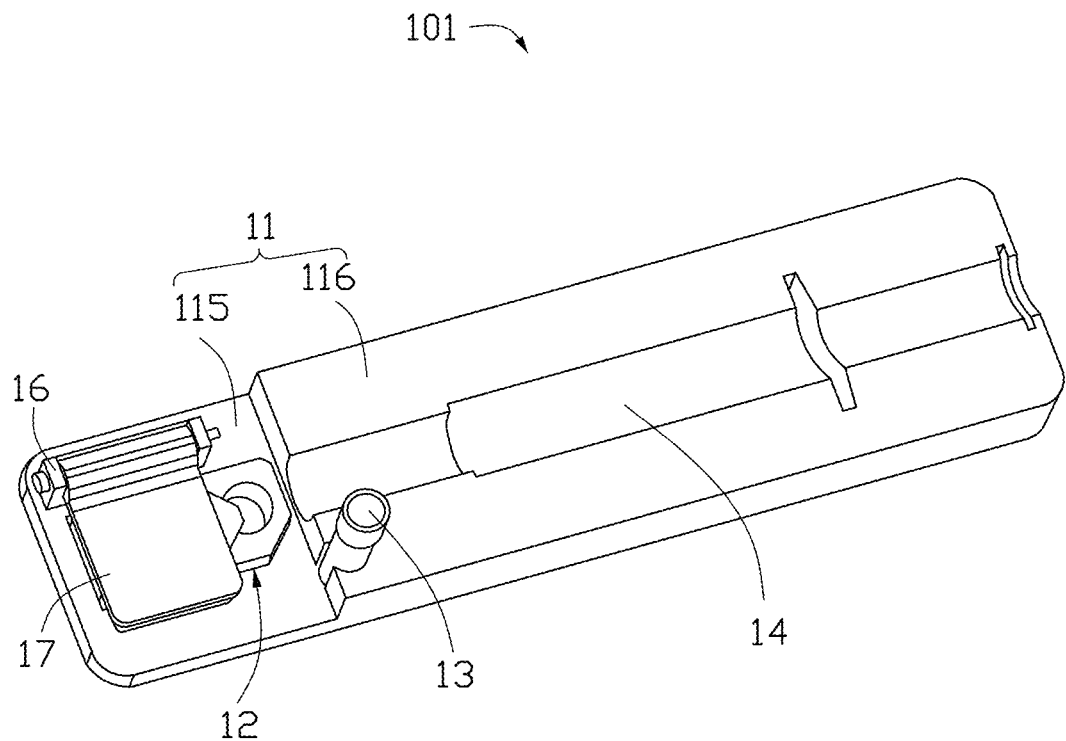
FIG. 18 is a diagrammatic view of a preparation platform in an eleventh embodiment according to the present disclosure.
Figure 19:
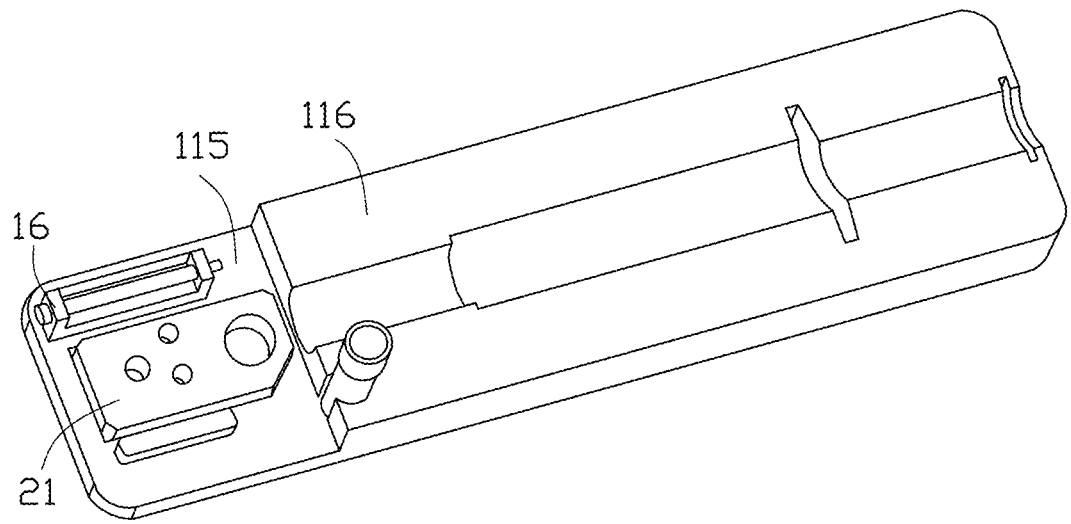
FIG. 19 is a diagrammatic view of another state of the preparation platform of FIG. 18.

FIGS. 18 and 19 show an isometric view of a preparation platform 101 in an eleventh embodiment according to the present disclosure. In the embodiment, the structure of the preparation platform 101 is substantially the same as that of the preparation platform 10 in the first embodiment. The difference is that when the pressure generation device is a negative pressure generation device, the base 11 of the preparation platform 101 includes a first portion 115 and a second portion 116 connected to the first portion 116. The first portion 115 is lower than the second portion 116. The droplet generation device slot 12 is disposed on the first portion 115. The power generation device slot 14 is disposed on the second portion 116. In other embodiments, when the collection container 30 is disposed in the chip body 21, the collection container slot 13 is absent from the second portion 116. The preparation platform 101 also includes a fixing seat 16 fixed on the first portion 115 and a dustproof cover 17 rotatably connected to the fixing seat 16. The dustproof cover 17 is disposed on one side of the chip body 21, and prevents dust from entering the chip body 21. In detail, the dustproof cover 17 is disposed above the continuous phase inlet and/or the dispersed phase inlet, or above the continuous phase reservoir and/or the dispersed phase reservoir.

Figure 20:
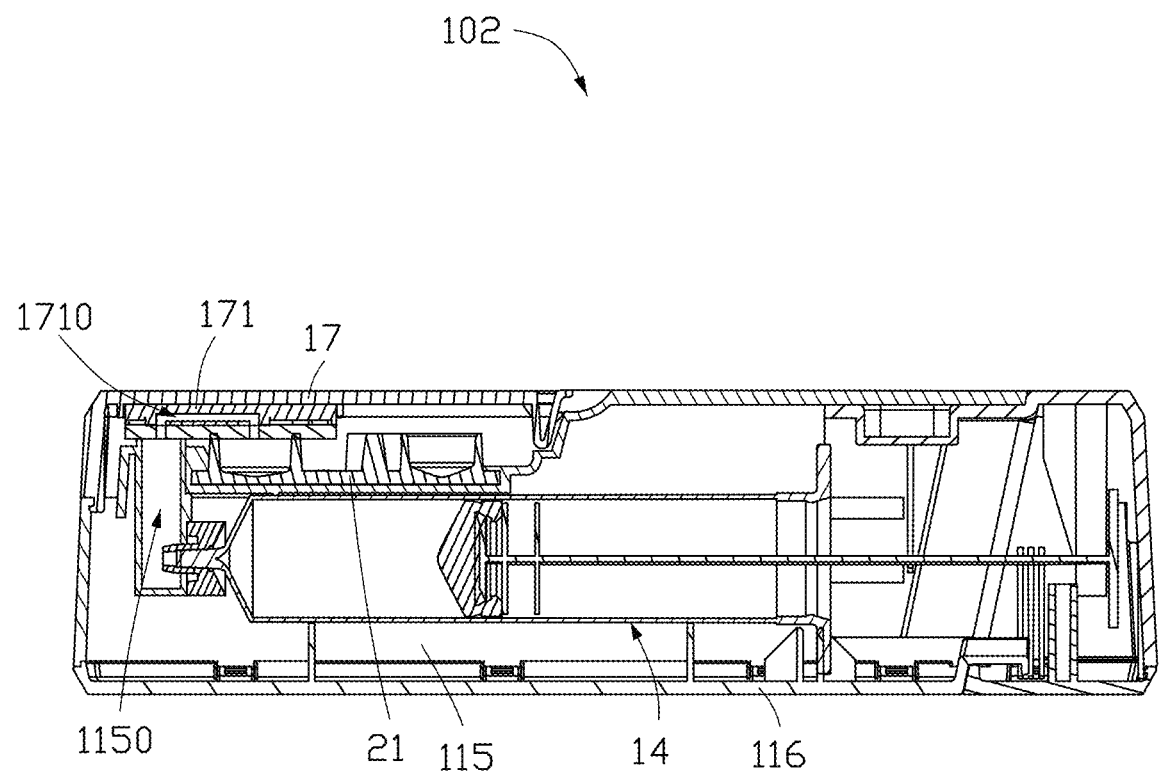
FIG. 20 is a diagrammatic view of a preparation platform in a twelfth embodiment according to the present disclosure.

FIG. 20 shows an isometric view of a preparation platform 102 in a twelfth embodiment according to the present disclosure. In the embodiment, the structure of the preparation platform 102 is substantially the same as that of the preparation platform 101 in the eleventh embodiment. The difference is that when the pressure generation device is a negative pressure generation device, the power generation device slot 14 is disposed inside the second portion 116 and further extends to the first portion 115. That is, a portion of the power generation device 50 is disposed inside the second portion 116, and the other portion is disposed inside the first portion 115.

A sealing cushion 171 is disposed between the dustproof over 17 and the chip body 21. The sealing cushion 171 covers the chip body 21 and prevents dust from entering the chip body 21. The sealing cushion 171 defines a first channel 1710 therein. The first portion 115 further defines a second channel 1150 connected between the first channel 1710 and the power generation device 50. Thus, the chip body 21 hermetically connects to the power generation device 50 through the first channel 1710 and the second channel 1150.

Figure 21:
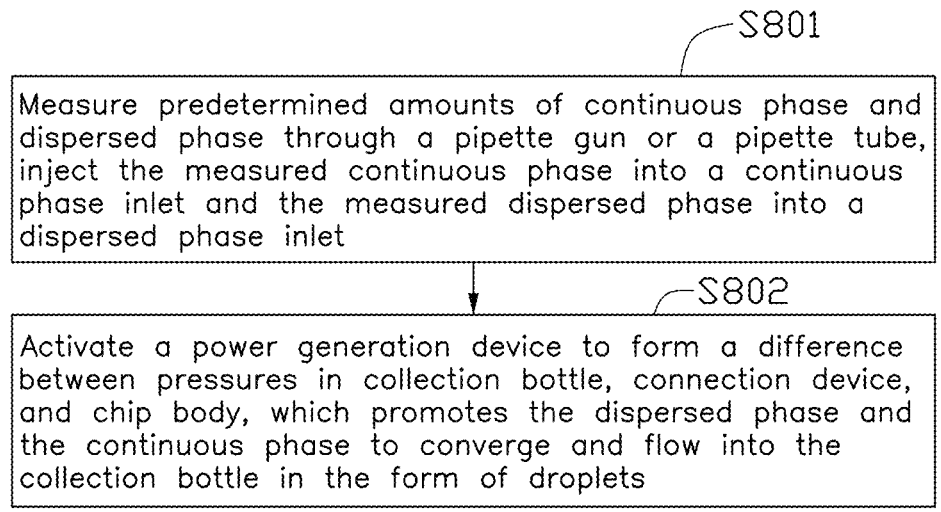
FIG. 21 is a flowchart of a method for preparing droplets using a microfluidic chip system without a vibration device.
Figure 22:
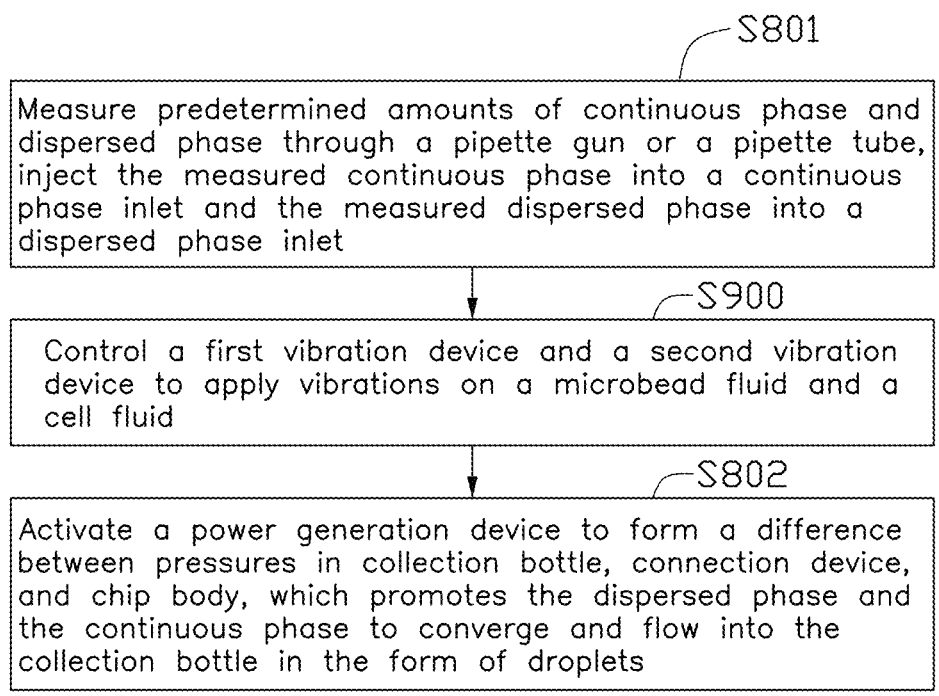
FIG. 22 is a flowchart of a method for preparing droplets using a microfluidic chip system with a vibration device.

FIGS. 21 and 22 illustrate an embodiment of a method for preparing droplets. The method can be performed by the microfluidic chip system 100 or a similar system. The method includes the following steps.

Step S801: predetermined amounts of continuous phase and dispersed phase are measured through a pipette gun or a pipette tube. The measured continuous phase is injected into the continuous phase inlet, and the measured dispersed phase is injected into the dispersed phase inlet.

In detail, in the embodiment, step S801 uses the pipette gun or the pipette tube to measure predetermined amounts of oil phase 80, cell fluid 60, and microbead fluid 70. The oil phase 80 is injected into the oil phase inlet in 213 of the microfluidic chip system 100. The cell fluid 60 is injected into the cell fluid inlet 214. The microbead fluid 70 is injected into the microbead fluid inlet 215.

When the microfluidic chip system 100 includes the continuous phase reservoir and the dispersed phase reservoir, step S801 uses the pipette gun or the pipette tube to measure predetermined amounts of continuous phase and dispersed phase. The measured continuous phase is injected into the continuous phase reservoir. The measured dispersed phase is injected into the dispersed phase reservoir.

In detail, in the embodiment, the microfluidic chip system 100 also includes the first reservoir 22, the second reservoir 23, and the third reservoir 24. Therefore, step S801 uses the pipette gun or the pipette tube to measure predetermined amounts of oil phase 80, cell fluid 60, and microbead fluid 70. The measured oil phase 80 is injected into the first reservoir 22. The measured cell fluid 60 is injected into the second reservoir 23. The measured microbead fluid 70 is injected into the third reservoir 24. The oil phase 80 from the first reservoir 22 enters the oil phase inlet in 213. The cell fluid 60 from the second reservoir 23 enters the cell fluid inlet 214. The microbead fluid 70 from the third reservoir 24 enters the microbead fluid inlet 215.

In the embodiment, the volume of the cell fluid 60 is 200 μL, the volume of the microbead fluid 70 is 200 μL, and the volume of the oil phase 80 is 400 μL.

The sequence for adding the cell fluid 60, microbead fluid 70, and the oil phase 80 can be first the cell fluid 60, then the microbead fluid 70, and finally the oiling phase 80. It can also be the microbead fluid 70 first, then the cell fluid 60, and finally the oiling phase 80. It can also be adding the cell fluid 60, the microbead fluid 70, and the oil phase 80 simultaneously.

Step S802: the power generation device 50 is activated to form a pressure difference between the collection container 30, the connection device 40, and the chip body 21, and atmospheric pressure. The difference in pressure promotes the dispersed phase and the continuous phase to converge and flow into the collection container 30 in the form of droplets.

In detail, step S802 is activating the power generation device 50, to cause a pressure difference between the collection container 30, the second pipe 42, and the droplet outlet 216, the converging channel 210, at least one dispersed phase guiding channel, the dispersed phase inlet, and the continuous phase inlet and atmospheric pressure. The difference in pressure promotes the continuous phase and the disperse phase to flow towards the converging channel 210 and form the droplets 200 under the converging channel 210. The droplets 200 further flow through the droplet outlet 216 and the second pipe 42, and enter the collection container 30 under the difference in pressure.

In the embodiment, step S802 can also be the activation of the power generation device 50, to cause a pressure difference between the collection container 30, the second pipe 42, and the droplet outlet 216, the converging channel 210, the microbead fluid guiding channel 219, the cell fluid guiding channel 218, the oil phase guiding channel 217, the microbead fluid inlet 215, the cell fluid inlet 214, the oil phase inlet 213 and the atmospheric pressure. The difference in pressure causes the cell fluid 60, the microbead fluid 70, and the oil phase 80 to flow towards the converging channel 210 and form the droplets 200 at the converging channel 210. The droplets 200 further flow through the droplet outlet 216 and the second pipe 42, and enter the collection container 30 under the pressure difference.

In the embodiment, the droplet generation device 20 of the microfluidic chip system 100 also includes the first reservoir 22, the second reservoir 23, and the third reservoir 24. Thus, step S802 can also be activating the power generation device 50, to cause a pressure difference between the collection container 30, the second pipe 42, and the droplet outlet 216, the converging channel 210, the microbead fluid guiding channel 219, the cell fluid guiding channel 218, the oil phase guiding channel 217, the third reservoir 24, the second reservoir 23, and the first reservoir 22 and the atmospheric pressure. The difference in pressure promotes the cell fluid 60, the microbead fluid 70, and the oil phase 80 to flow towards the converging channel 210 and form the droplets 200 at the converging channel 210. The droplets 200 further flow through the droplet outlet 216 and the second pipe 42, and enter the collection container 30 under the pressure difference.

In the embodiment, the power generation device 50 can be a negative pressure generation device. Thus, step S802 can also be activating the power generation device 50, to cause a negative pressure to generate in the collection container 30, the second pipe 42, and the droplet outlet 216, the converging channel 210, the microbead fluid guiding channel 219, the cell fluid guiding channel 218, and the oil phase guiding channel 217. The negative pressure causes the cell fluid 60, the microbead fluid 70, and the oil phase 80 to flow towards the converging channel 210 and form the droplets 200 at the converging channel 210. The droplets 200 further flow through the droplet outlet 216 and the second pipe 42, and enter the collection container 30 under the pressure difference. Furthermore, the negative pressure can be generated by pulling the operation portion 52 of the power generation device 50 to a predetermined position, and limiting the first limiting member 54 in the first limiting slot 15 of the base 11.

In other embodiments, the power generation device 50 may also be a positive pressure generation device. Thus, step S802 can also be activating the power generation device 50, to cause a positive pressure to generate in the dispersed phase guiding channel, the continuous phase guiding channel, the droplet outlet 216, and the collection container 30. The positive pressure prompts the cell fluid 60, the microbead fluid 70, and the oil phase 80 to flow towards the converging channel 210 and form the droplets 200 at the converging channel 210. The droplets 200 further flow through the droplet outlet 216 and enter the collection container 30 under the positive pressure.

Referring to the FIG. 19, in another embodiment, before starting the power generation device 50, the method further includes step S900: the first vibration device 25 and the second vibration device 26 apply vibrations on the microbead fluid 70 and the cell fluid 60. For example, power switches (not shown) of the first vibration device 25 and the second vibration device 26 set on the base of 11 are turned on, to cause the first described vibration device 25 and the second vibration device 26 to generate vibrations and agitation in the microbead fluid 70 and the cell fluid 60.

Since the microfluidic chip system 100 may include only one vibration device, step S900 in another embodiment may also be at least one vibration device applying vibration on the microbead fluid 70 and/or the cell fluid 60.

In other embodiments, step S900 may also be the first vibration device 25 and the second vibration device 26 applying vibrations on the dispersed phase. For example, the power switches (not shown) of the first and second vibration devices 25 and 26 set on the base 11 are turned on, to cause the first vibration device 25 and the second vibration device 26 to apply vibrations on the dispersed phase.

In the microfluidic chip system of the present disclosure, 1) the droplet generation device, the power generation device, and the collection container are fixed to the preparation platform, to ensure the stability of the generation of droplets by the microfluidic chip system. 2) a single power source is arranged at the droplet outlet of the droplet generation device to form a vacuum in the droplet generation device, which facilitates simultaneous flows of the cell fluid, the microbead fluid, and the oil phase in the droplet generation device. A high flux and a high degree of uniformity of the droplets are obtained. 3) When the injection device is used as the power source, the position of the operation portion of the injection device is controlled according to the ideal gas state equation of $P_1V_1=P_2V_2$, and the first limiting portion of the injection device is limited at the predetermined position by the first limiting slot of the base, to maintain the vacuum. The cost is low, and the device is easy to operate. 4) The pressure in the power generation device changes when the reagents are injecting and flowing. The reagents infill the collection device, and the pressure change in the power generation device also follows the ideal gas state equation. 5) The reduction of pressure in the droplet generation device, the flow rates of the continuous and the dispersed phase, and the size and the generation frequency of the droplets are predictable, programmable, and reproducible. 6) The vibration device of the microfluidic chip system can effectively decrease the sedimentation of cell fluid and/or microbead fluid during experiment, so as to ensure a homogenous concentration in the cell fluid and/or the microbead fluid.

In addition, the microfluidic chip system according to the present disclosure can prepare 250,000 droplets within 2 minutes, which means that 10,000 single-cell target products can be obtained. A droplet contains a magnetic bead and a cell, and the period of generation of the droplet can be adjusted as needed to control the number of the target products. The entire size of the microfluidic chip system is the same as that of the iPad Mini by Apple, which allows additional space for users.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present exemplary embodiments, to the full extent indicated by the plain meaning of the terms in which the appended claims are expressed.

What is claimed is:

1. A microfluidic chip system for generating droplets, comprising:
   a droplet generation device for generating the droplets;

a power generation device for supplying a power to the droplet generation device, the power generation device comprising a main body, an operation portion, and a first limiting member, an end of the operation portion received in the main body, another end of the operation portion exposed from the main body and connected to the first limiting member;

a collection container for collecting the droplets flowing out of the droplet generation device;

a connection device connecting the droplet generation device, the power generation device, and the collection container to each other, and a preparation platform for supporting the droplet generation device, the power generation device, and the collection container, wherein the preparation platform comprises a base, the base defines a droplet generation device slot, a power generation device slot, and a first limiting slot, the base comprises a first surface, a second surface opposite to the first surface, and a first sidewall connected between the first surface and the second surface, the droplet generation device slot and the power generation device slot are recessed from the first surface, the first limiting slot is recessed from the first surface and the first sidewall, the droplet generation device is received in the droplet generation device slot, the main body and the operation portion are received in the power generation device slot, and the first limiting slot is configured to receive the first limiting member and keep the first limiting member at a predetermined location.

2. The microfluidic chip system of claim 1, wherein the droplet generation device comprises a chip body, the chip body defines a continuous phase inlet and a dispersed phase inlet, the continuous phase and the dispersed phase enter the chip body through the continuous phase inlet and the dispersed phase inlet.

3. The microfluidic chip system of claim 2, wherein the microfluidic chip system further comprises a continuous phase reservoir and a dispersed phase reservoir, the continuous phase reservoir and the dispersed phase reservoir are fixed on or disposed outside the chip body.

4. The microfluidic chip system of claim 2, wherein the collection container is fixedly received in the chip body, and the chip body is fixedly received in the droplet generation device slot.

5. The microfluidic chip system of claim 2, wherein the microfluidic chip system further comprises at least one vibration device, the vibration device is received in the droplet generation device slot and corresponds to the dispersed phase inlet, and the vibration device is configured to apply vibration to the dispersed phase.

6. The microfluidic chip system of claim 2, wherein the microfluidic chip system also comprises at least one vibration device, the vibration device is disposed on the chip body and corresponds to the dispersed phase inlet, and the vibration device is configured to apply vibration to the dispersed phase.

7. The microfluidic chip system of claim 2, wherein the power generation device is a positive pressure generation device, and the positive pressure generation device connects to the continuous phase inlet and the dispersed phase inlet through the connection device.

8. The microfluidic chip system of claim 1, wherein the base comprises a first portion and a second portion connected to the first portion, the first portion is lower than the second portion, the droplet generation device slot is formed on the first portion, and the power generation device slot is formed on the second portion.

9. The microfluidic chip system of claim 1, wherein the collection container is disposed outside the droplet generation device, the base further defines a collection container slot, the collection container slot is recessed from the first surface, and the collection container is fixedly received in the collection container slot.

10. The microfluidic chip system of claim 1, wherein the collection container is disposed on and integrally formed with the droplet generation device.

11. The microfluidic chip system of claim 1, wherein the power generation device is an injection device.

12. The microfluidic chip system of claim 1, wherein the power generation device is a negative pressure generation device, and the negative pressure generation device connects to the collection container through the connection device.

13. The microfluidic chip system of claim 12, wherein the preparation platform further comprises a fixing seat and a dustproof cover rotatably connected to the fixing seat, the dustproof cover is disposed on one side of the droplet generation device, and the dustproof cover is configured to prevent dust from entering the droplet generation device.

* * * * *